(12) United States Patent
Wellnhofer

(10) Patent No.: US 7,815,576 B2
(45) Date of Patent: Oct. 19, 2010

(54) METHOD FOR DETERMINING HAEMODYNAMIC PARAMETERS

(75) Inventor: Ernst Wellnhofer, Berlin (DE)

(73) Assignee: Deutsches Herzzentrum Berlin, Berlin (DE)

( * ) Notice: Subject to any disclaimer, the term of this patent is extended or adjusted under 35 U.S.C. 154(b) by 1215 days.

(21) Appl. No.: 10/571,950

(22) PCT Filed: Feb. 16, 2005

(86) PCT No.: PCT/DE2005/000304

§ 371 (c)(1),
(2), (4) Date: Mar. 13, 2006

(87) PCT Pub. No.: WO2005/082243

PCT Pub. Date: Sep. 9, 2005

(65) Prior Publication Data

US 2008/0255466 A1    Oct. 16, 2008

(30) Foreign Application Priority Data

Feb. 26, 2004  (DE) .................. 10 2004 009 871

(51) Int. Cl.
*A61B 5/00* (2006.01)
(52) U.S. Cl. .................. 600/485; 600/490; 600/500; 600/486
(58) Field of Classification Search .................. None
See application file for complete search history.

(56) References Cited

U.S. PATENT DOCUMENTS 5,865,758 A * 2/1999 Louzianine .................. 600/504
6,290,652 B1   9/2001 Wellnhofer
2004/0024294 A1   2/2004 Wellnhofer

FOREIGN PATENT DOCUMENTS

DE    198 20 844 A1    6/1999
DE    100 49 734 A1    4/2002

OTHER PUBLICATIONS

International Search Report, dated Jun. 28, 2005, corresponding to PCT/DE2005/000304.
International Preliminary Report on Patentability dated Oct. 4, 2006 for corresponding PCT application No. PCT/DE2005/000304.

* cited by examiner

*Primary Examiner*—Robert L Nasser
(74) *Attorney, Agent, or Firm*—Christie, Parker & Hale, LLP

(57) ABSTRACT

A method for determining haemodynamic parameters from patient pressure signals includes receiving patient pressure signals from a measurement receiver to which vessel pressures measured in the body of a patient are supplied, selecting and determining a patient pressure signal as reference pressure signal from the patient pressure signals sent from the measurement receiver, dividing the patient pressure signals and reference pressure signal into segments, and examining these segments for artifacts with methods in the time range by using the first derivative with respect to time of the pressure signals wherein artifact afflicted segments are discarded. The method further includes determining the start and end of a heart beat by the reference pressure signal and using the non-discarded segments of the patient pressure signals for calculating haemodynamic parameters.

10 Claims, 4 Drawing Sheets

METHOD FOR DETERMINING HAEMODYNAMIC PARAMETERS

CROSS-REFERENCE TO A RELATED APPLICATION

This application is a National Phase Patent Application of International Application Number PCT/DE2005/000304, filed on Feb. 16, 2005, which claims priority of German Patent Application Number 10 2004 009 871.9, filed on Feb. 26, 2004.

BACKGROUND

The invention relates to a method for determining haemodynamic parameters from patient pressure signals.

For the invasive, intra-arterial and intravenous pressure measurement in cardiology, intensive medicine and anaesthesia transfer systems are used in which the pressure measurement is carried out in the body of a patient and transferred through the transfer system, which is designed for example as a catheter, to a storage medium set away from the patient body.

There is therefore the need to both store and analyse the transferred data. It is particularly of interest to determine from the incoming data haemodynamic parameters from which a doctor can deduce his diagnosis.

There is frequently the problem that the incoming signals originating in the body of the patient are subject to errors (artifacts). Such errors arise in particular in dependence on the length, cross-section, structure and properties of the catheter material. This can lead to resonances, attenuations and energy losses in the detected measured pressure value which ultimately leads to a falsification of the patient signal.

One method for correcting such artifacts which are conditioned through the transfer system, is known from German Patent Application No. DE 198 20 844 A1; one method for determining and monitoring the transfer function of the transfer system is described in German Patent Application No. DE 100 49 734 A1.

However artifacts also often occur which are not conditioned by transfer errors, such as for example motion artifacts which happen through manipulation on the catheter or knocking of the catheter in the vessel or through a break in the pressure measurement when changing the catheter or injection, as well as such artifacts which arise on flushing through the system. The haemodynamic parameters which are calculated from such falsified patient signals can thus not provide the doctor with a suitable foundation on which to base his diagnosis.

The object of the present invention is therefore to provide a method for determining haemodynamic parameters from patient pressure signals in which the determination is only carried out on the basis of suitable signals.

BRIEF DESCRIPTION

The method according to the invention for determining haemodynamic parameters from patient pressure signals comprises the following steps:
a) receiving patient signals from a measurement receiver which is supplied with vessel pressures measured in the body of a patient;
b) selecting and determining a patient pressure signal as reference pressure signal from the patient pressure signals sent from the measurement receiver;
c) dividing the patient pressure signals and reference pressure signal into segments;
d) examining these segments for artifacts with methods in the time and frequency range by using the first derivative with respect to time of the pressure signals whereby artifact-afflicted segments are discarded;
e) determining the beginning and end of a heart beat with the aid of the reference pressure signal and
f) using the non-discarded patient pressure signal segments for calculating haemodynamic parameters.

After receiving patient signals through a measured value receiver according to step a) and before selecting and determining a patient pressure signal as reference pressure signal from the patient pressure signals sent by the measured value receiver according to step b) it is possible to carry out where required a preliminary processing of the signals for correcting the artifacts conditioned through the transfer system using the methods described in German Patent Application No. DE 198 20 844 A1 and German Patent Application No. DE 100 49 734 A1. The artifacts conditioned through the transfer system are thereby corrected.

By selecting and determining a patient pressure signal as reference pressure signal according to step b) it is ensured that a reliable stable recognition of the heart beats is carried out.

The division of the patient pressure signals and reference pressure signals into segments according to step c) enables a high-resolution examination and processing of the pressure signals in the following steps.

Step d) serves to identify motion artifacts, rinsing artifacts and/or other flagrant mechanical artifacts, as well as signal breaks and noise artifacts for each signal, including the reference signal. For this an investigation is made into the relevant deviation of the derivative of the signal from for example a smoothed copy of the relevant signal, or the differences of mean, minimum and maximum, the deviation of the signal from a regression line and further analyses in the time and frequency range. By separating out flagrant artifacts it is ensured that only suitable patient pressure signal segments are included for calculating haemodynamic parameters.

There are basically two possibilities for determining artifacts, namely both segment-wise and beat-wise.

By one segment is thereby meant a specific time section which is to be defined and in which the relevant pressure signal is considered. One segment can thereby comprise for example 500 ms. For a beat-wise artifact determination, on the other hand, a time section is used which corresponds to one beat period.

Fixing the time of the beginning and end of a heart beat with the aid of the reference pressure signal according to step e) enables the local search for the start and end of the corresponding heart beat from other patient pressure signals.

The non-discarded patient pressure signal segments can now serve according to step f) for calculating haemodynamic parameters which are based on unfalsified pressure data.

As will be described below different haemodynamic parameters can be calculated with the aid of the method according to the invention. More particularly the patient pressure signals and/or reference pressure signals are used as the basis for determining the type of signal, determining the cardiac output, determining the beat at the reference signal, for an evaluation typical of the type of signal and for a low frequency analysis (of the so-called Mayer waves).

1. Beat Determination on the Reference Signal

A threshold value determination dependent on the type of signal takes place for the derivative of the pressure according to time. By a flooding algorithm a search is made for the peaks of this derivative, followed by an examination whether it is a local maximum. For this, the second derivative is investigated in a local surrounding. Finally a check is carried out for plausibility dependent on the type of signal.

The determination of the start and end of the beat is then carried out in the other signals using the results of this first step.

2. Determining the Type of Signal (Facultative)

Based on the time definition of the length of the heart beat, an investigation is made from the relevant pressure signals and their first and second derivative according to time of corresponding sections in order to identify the type of signal whereby it is possible to use as signal type for example the left-ventricular, systemic arterial, pulmonal-arterial, right-ventricular, right-atrial or pulmonal-capillary closure pressure. For the purpose of identifying the type of signal a feature extraction is carried out by determining in addition to the pulsatility index, the maximum derivative of the pressure according to time, statistical parameters (medians, mean values and moments as well as parameters from the Fourier transformation of the beat curve and their derivatives. Further features are obtained from breaking down the curve into two halves relative to the time axis and/or an investigation of higher moments or cumulants of the curve in the complex graph. The time axis thereby forms the real part and the pressure the imaginary part of the complex graph.

Determining the type of signal is carried out by combining a score system, a stepwise logistic regression and/or a discriminant analysis and plausibility check. The logistic regression or discriminant analysis uses both values from the time range and also characteristics of the Fourier transformation of the relevant beat.

3. Cardiac Output Determination

Determining the cardiac output also takes place based on the time definition of a heart beat length.

The determination algorithm for determining a cardiac output thereby has a facultative measuring-position-dependent multiple regression for resistance, beat volume and cardiac output, a plausibility check as well as a fine correction. The multiple regression uses both values from the time range and also characteristics of the Fourier transformation of the relevant beat. This is thereby not a pulse contour analysis.

4. Evaluation Typical of a Signal Type

Specific haemodynamic parameters are calculated in dependence on the type of pressure signals measured.

The calculation of the following parameters is thus possible for ventricle pressure signals:

Systolic, minimal and endiastolic pressures, maximum and minimum of the derivative of the pressure according to time, time tension index (TTI), maximum shortening speed (VPM), developed pressure, pulsatility, relaxation time (tau).

For artery pressures it is possible to determine systolic, diastolic and mean pressure, as well as maximum and minimum of the derivative of the pressure according to time. Furthermore ejection time, pulse pressure and a pulsatility index can also be calculated.

V-wave, A-wave, maximum, minimum and mean pressure can be determined for auricle pressures.

5. Low Frequency Analysis (Mayer Waves)

For low frequency analysis a power spectrum estimation is carried out by an eigenvalue process (with four to six sub chambers). The power spectrum thus obtained is logarithmed. A further power spectrum estimation by an eigenvalue process (with two sub chambers) supplies a severely smoothed spectrum which represents substantially the very low frequency component. The logarithmed very low frequency component is subtracted from the logarithmed total power spectrum power. The very low frequency component is thereby removed.

Then two maxima and the minimum in between are then identified. The positions of the low frequency component and the high frequency component are identical with those of the delogarithmed residual spectrum after removing the very low frequency component.

A delogarithmization of the residual spectrum and a determination of the power integral of the low and high frequency components are then carried out.

To determine the type of signal advantageously an analysis of the first derivative according to time is then carried out whereby the function f2 of the reference pressure signal is dependent on the time. To calculate the cardiac output as haemodynamic parameter the first and second derivative of a function f1 is determined according to the time whereby the function f1 of the patient pressure signals is dependent on the time.

The determined haemodynamic parameters can advantageously be stored on a output unit more particularly an electronic data medium such as a memory disc, network or patient information system and/or displayed on a monitor. The parameters can furthermore be transferred directly into a patient information system.

In one development of the invention the method has an automatic identification based on a logistical analysis of the type of the measured patient pressure, more particularly a pressure of the left ventricle, the aorta, the right ventricle, the pulmonal artery, the pulmonal capillary closure pressure as well as the right auricle.

BRIEF DESCRIPTION OF THE DRAWINGS

The method according to the invention for determining haemodynamic parameters will be explained in further detail with reference to the drawings.

DETAILED DESCRIPTION

Figure 1:
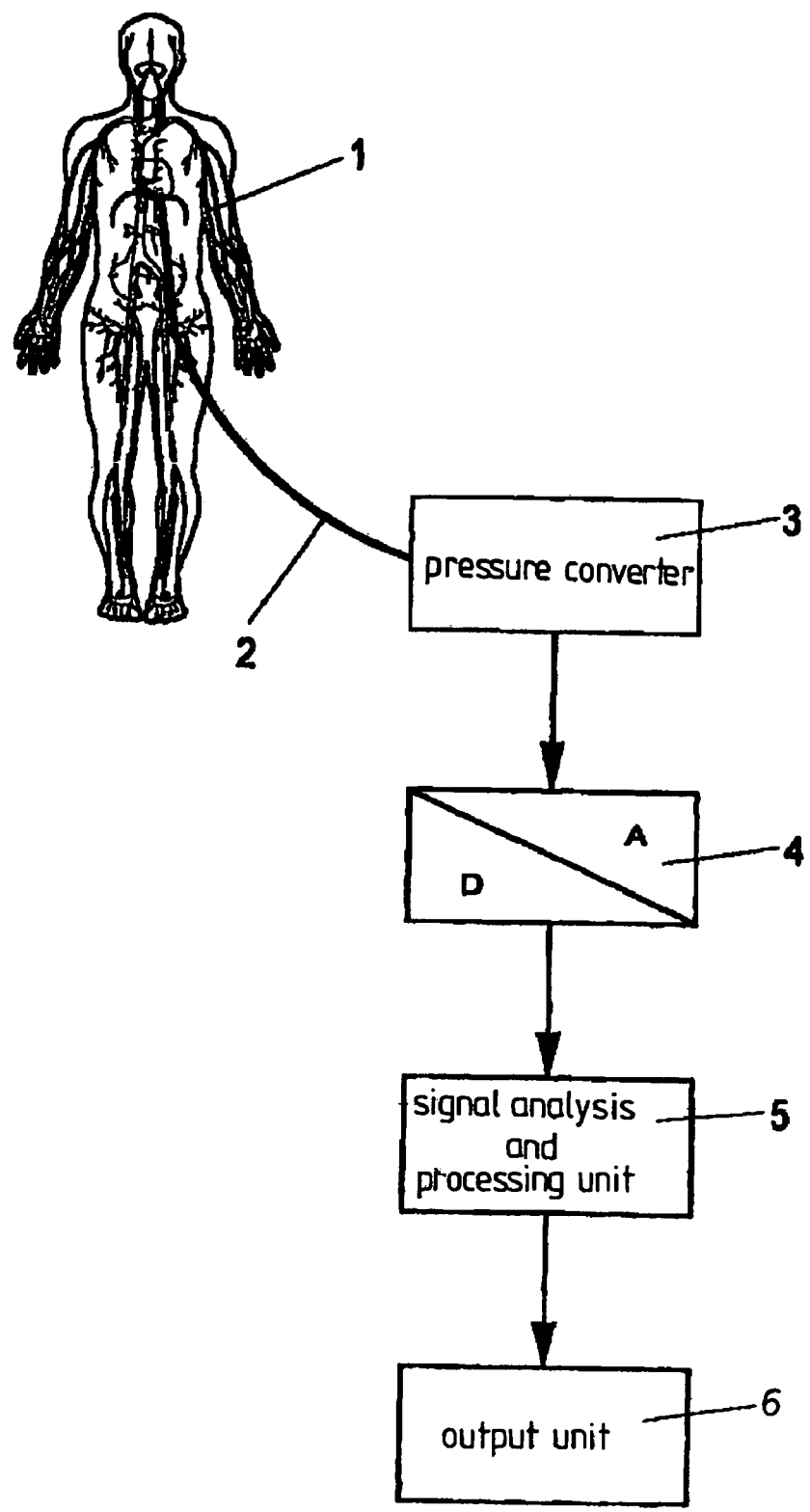
FIG. 1 is a block circuit diagram of a device which is suitable for carrying out the method for determining haemodynamic parameters.

FIG. 1 shows the principle structure of an invasive pressure measurement wherein a catheter 2 forming the transfer system is moved through the venous or arterial system of a patient 1 into the vicinity of the point where the pressure measurement is to be performed. A pressure converter 3 generates in dependence on the patient pressure signals electrical signals which are supplied to an analog/digital converter 4. The signals converted in the analog/digital converter 4 are then forwarded to a measurement receiver in the form of a signal-analysis and processing unit 5 in which the method according to the invention for determining haemodynamic parameters is carried out. The calculated haemodynamic parameters are then forwarded to an output unit 6 more particularly in the form of an electronic data medium or monitor.

Figure 2:
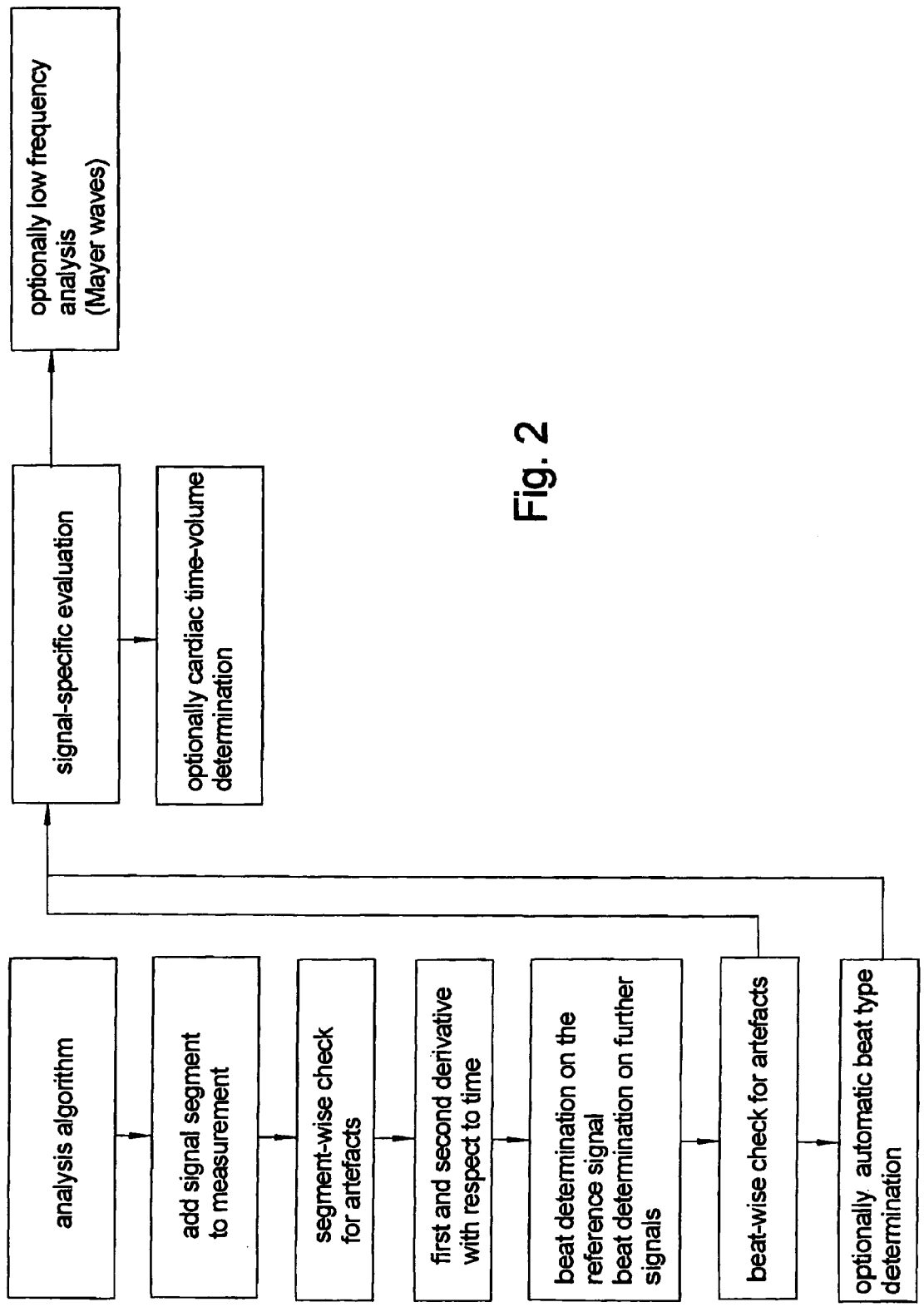
FIG. 2 is a flow chart of the method for determining haemodynamic parameters.

FIG. 2 shows a flow chart of the method for determining haemodynamic parameters.

According to this method, first a selection of a patient pressure signal as a reference pressure signal is carried out from the received patient pressure signals. After dividing the patient pressure signals and the reference pressure signal into segments, a check is made on these segments for artifacts with processes in the time and where necessary frequency range. For this the first and second derivative of the pressure signals is determined according to time.

A beat determination is then carried out on the reference signal and/or on further signals. A beat-wise examination of the artifacts is then carried out on the basis of the length of a heat beat. Such artifacts are for example motion artifacts which arise through manipulation on the catheter, knocking of the catheter in the vessel, interruption in the pressure measurement when changing catheter, injection or flushing of the system. Those segments which are identified as afflicted with artifacts are discarded. As an optional measure an automatic beat type determination can now be carried out.

A signal-specific evaluation is carried out on the basis of the beat-wise artifact examination. A cardiac output determination and/or low frequency analysis are optionally carried out.

The calculated haemodynamic parameters can be displayed on an output unit e.g. a monitor. In an advantageous embodiment of the invention the results can be integrated into the digital patient files and/or an automatic findings report or text processing to the doctor's notes.

Figure 3:
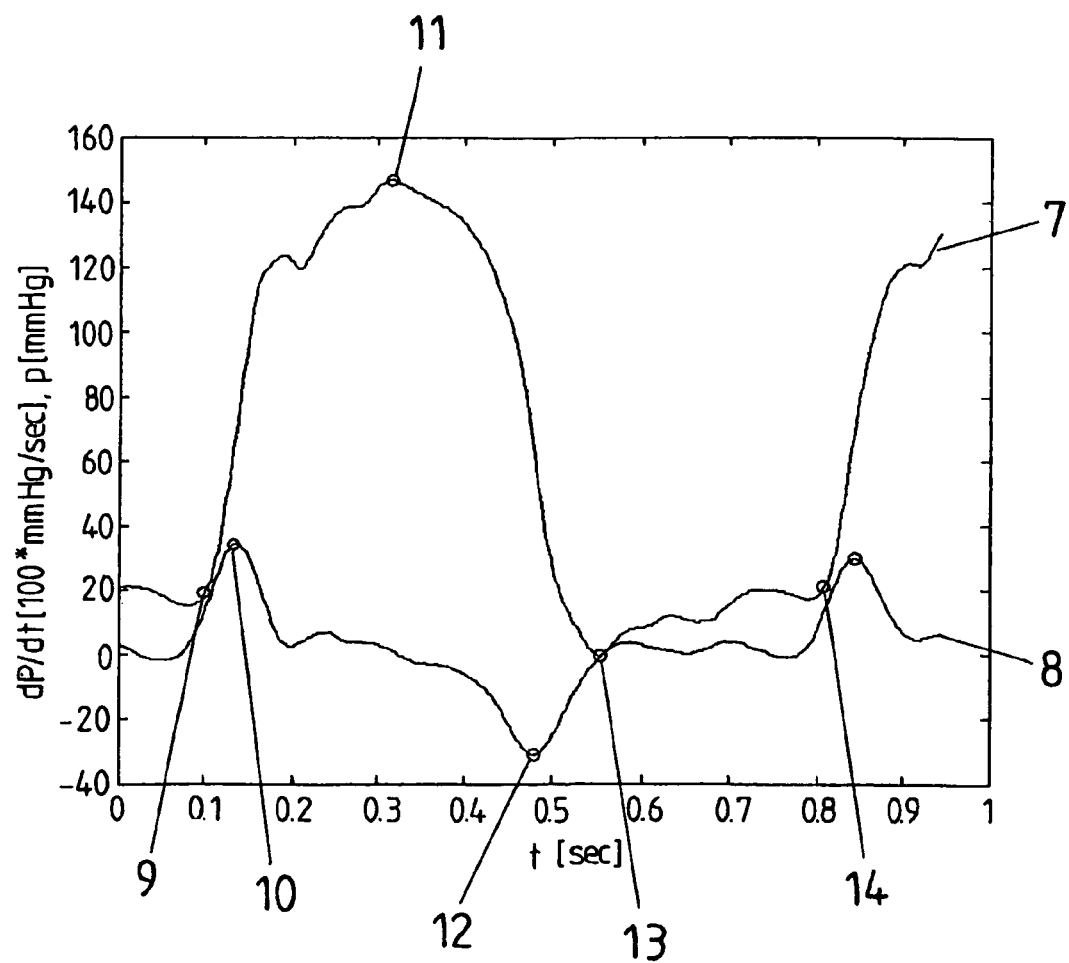
FIG. 3 is a graphic representation of the first derivative of the pressure signal of the left ventricle over time.

FIG. 3 shows a graphic representation of a left ventricular (LV) patient pressure signal 7 and the associated first derivative 8 over time. On the abscissa is entered the time in seconds, on the ordinate the pressure in millimeters mercury column (mmHg) and the first derivative of the pressure according to time in millimeters mercury column per second (mmHg/sec), scaled down by factor 0.01 for graphic reasons.

Different haemodynamic parameters are determined using the method according to the invention. Patient pressure signals are thereby received from a measurement receiver which measures vessel pressures in the body of the patient.

After checking for (flagrant) artifacts only patient pressure signal segments with sufficient quality are analyzed. After selecting and determining a patient pressure signal as reference pressure signal from the patient pressure signals 7 sent by the measurement receiver, the time range of one heart beat is found and the start and end of the heart beat around this time is determined on the actual patient pressure signal. In the illustrated case the reference signal was a femoral pressure signal.

The ventricle beat precedes a beat of this reference signal. The maximum of the first derivative of the ventricle pressure signal beat within a time vicinity (e.g. 100 ms) of the maximum of the first derivative of the femoral pressure signal beat is sought and then starting from this point the beginning of the steep rise of the ventricle pressure signal is sought (end diastole of the previous beat, 9). The end of the beat is thus precisely determined. After determining the heart beat at the actual pressure signal a beat wise examination of artifacts still takes place once more.

The non-discarded patient pressure signals are used for calculating haemodynamic parameters. The curve shows the result of an automatic analysis. The beat starts at the rise of the pressure curve with the end diastole of the previous beat 9. The maximum of the derivative 10 is located at the point of the steepest rise. The next points to follow in time sequence are the systolic maximum 11 of the pressure, the minimum 12 of the derivative at the steepest drop in pressure, the minimum of the pressure 13 in the beat range and the end diastole 14 of the actual beat. From the beat length is calculated the heart frequency (HF) at for example 85 beats per minute, from the beat is furthermore determined the mean pressure at 67 mmHg, the developed pressure (DP) as pressure maximum minus end-diastolic pressure at 127 mmHg, the dimension-less pulsatility index (PI) as pressure amplitude through mean pressure at 2, 1999, the relaxation time (tau) according to five different methods known to the expert from literature at tau=16 msec, the maximum shortening speed (VPM) after a calculation likewise known to the expert at VPM=2,8478 Hz and the time tension index (TTI) as integral of the pressure in the systole at TTI=44,7269 mmHg*sec.

The calculated parameters can then be displayed on an output unit 6 as data files, on the screen or on a monitor.

Figure 4:
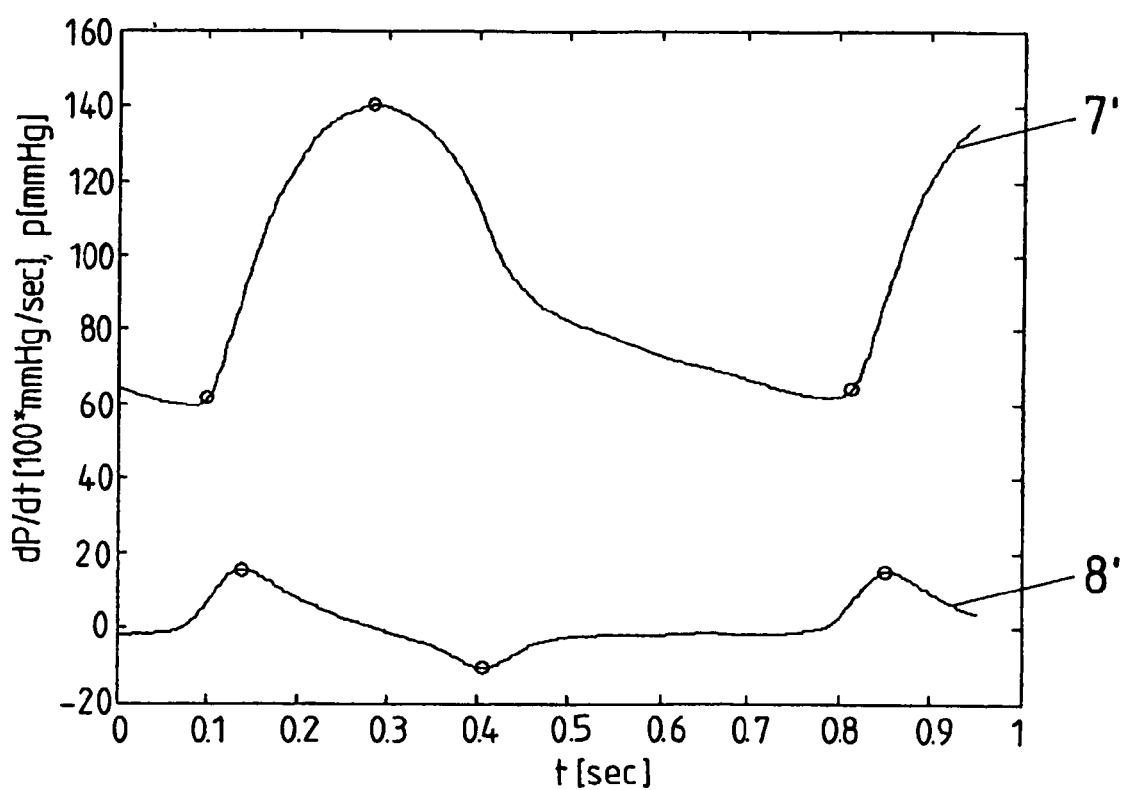
FIG. 4 is a graphic representation of the first derivative of the pressure signal of the aorta over time.

FIG. 4 shows a graphic representation of a patient pressure signal 7' from the aorta (AO) and the associated first derivative 8' over time. On the abscissa is entered the time in seconds, on the ordinate the pressure in millimeter mercury column (mmHg) and the first derivative of the pressure according to time in millimeter mercury column per second (mmHg/sec), scaled down by factor 0.01 for graphic reasons.

The beat identification, automatic analysis and representation corresponds to the beat identification, automatic analysis and representation described in connection with FIG. 2. Instead of the developed pressure, with arterial pressures the pulse pressure (PP) and the ejection time (ET) in milliseconds (msec) are determined.

A calculation of the beat volume (ml/min), the cardiac output (CO) in liters per minute (l/min) and the system resistance (Res) is provided facultatively.

In the illustrated example the following haemodynamic parameters are calculated: the pulse pressure is determined at PP=76 mmHg, the ejection time amounts to ET=306 msec, the cardiac output CO=7 l/min and the system resistance result at Res=13.4 Wood units. Furthermore a heart frequency HF is calculated as 84 beats per minute. The mean pressure is determined at 94 mmHg and the dimension-less pulsatility index (PI) is determined at 0.83076.

The invention claimed is:

1. A method for determining haemodynamic parameters from patient pressure signals, the method comprising:
    a) receiving patient pressure signals from a measurement receiver to which vessel pressures measured in the body of a patient are supplied;
    b) selecting and determining a patient pressure signal as a reference pressure signal from the patient pressure signals sent from the measurement receiver;
    c) dividing the patient pressure signals and the reference pressure signal into segments;
    d) examining the patient pressure signal segments and the reference pressure signal segments in a time range for artifacts with time range methods by using a first derivative with respect to time of the patient pressure signals and the reference pressure signal wherein artifact-afflicted segments are discarded;
    e) determining a start and end of a heart beat on at least one of the patient pressure signals using the reference pressure signal; and
    f) using non-discarded segments of the patient pressure signals for calculating haemodynamic parameters.

2. The method according to claim 1, wherein the examination of the segments for artifacts is carried out with time range methods and frequency range methods.

3. The method according to claim 1, wherein an analysis of the first derivative with respect to time is carried out for determining signal type.

4. The method according to claim 1, wherein for determining signal type, a discriminant analysis or logistic regression is carried out based on beat-wise analysis of the patient pressure signals in time and frequency ranges.

5. The method according to claim 1, wherein to calculate beat volume as haemodynamic parameters, a beat-wise multiple regression based on parameters from standardized Fourier transformation and analysis of the patient pressure signals and derivatives of the parameters is undertaken in the time range.

6. The method according to claim 5, wherein at least one of size, weight, sex, and age is used for calibrating the beat volume as a haemodynamic parameter.

7. The method according to claim 1, wherein a signal-type evaluation is carried out to determine a type of measured pressure signal.

8. The method according to claim 1, wherein a low frequency analysis is carried out on the pressure signals.

9. The method according to claim 1, wherein the calculated haemodynamic parameters are stored electronically or displayed on an output unit.

10. The method according to claim 9, wherein the haemodynamic parameters are displayed on a monitor.

* * * * *